United States Patent
Stapley et al.

(10) Patent No.: US 11,999,687 B2
(45) Date of Patent: Jun. 4, 2024

(54) METHODS FOR THE PRODUCTION OF L-THREONIC ACID SALTS FROM L-XYLONIC ACID

(71) Applicant: DFI USA, LLC, Greenacres, WA (US)

(72) Inventors: Jonathan Stapley, Mercer Island, WA (US); David Genders, Lancaster, NY (US)

(73) Assignee: DFI USA, LLC, Greenacres, WA (US)

(*) Notice: Subject to any disclaimer, the term of this patent is extended or adjusted under 35 U.S.C. 154(b) by 0 days.

(21) Appl. No.: 18/042,950

(22) PCT Filed: Aug. 27, 2021

(86) PCT No.: PCT/US2021/048057
§ 371 (c)(1),
(2) Date: Feb. 24, 2023

(87) PCT Pub. No.: WO2022/047231
PCT Pub. Date: Mar. 3, 2022

(65) Prior Publication Data
US 2023/0227395 A1  Jul. 20, 2023

Related U.S. Application Data

(60) Provisional application No. 62/706,632, filed on Aug. 28, 2020.

(51) Int. Cl.
*C07C 51/235* (2006.01)
*C07C 45/51* (2006.01)
*C07C 51/47* (2006.01)
*C25B 3/07* (2021.01)

(52) U.S. Cl.
CPC .......... *C07C 51/235* (2013.01); *C07C 45/512* (2013.01); *C07C 51/47* (2013.01); *C25B 3/07* (2021.01)

(58) Field of Classification Search
CPC ..... C07C 51/235; C07C 45/512; C07C 51/47; C07C 47/19; C07C 59/10; C25B 3/07
See application file for complete search history.

(56) References Cited

U.S. PATENT DOCUMENTS

| 4,968,716 A * | 11/1990 | Markham ............ A61K 31/365 514/567 |
| 6,894,199 B2 * | 5/2005 | Heikkila .................. C12P 7/58 568/864 |
| 7,955,489 B2 | 6/2011 | Stapley et al. |
| 9,023,182 B1 * | 5/2015 | Cooper .................. B01J 19/087 204/157.68 |
| 9,702,047 B2 * | 7/2017 | Stapley ...................... C25B 3/00 |
| 2004/0254368 A1 * | 12/2004 | Togashi ................... C07H 1/00 536/124 |
| 2016/0194765 A1 * | 7/2016 | Genders .................... C25B 3/25 205/344 |
| 2019/0328689 A1 | 10/2019 | Liu et al. |

FOREIGN PATENT DOCUMENTS

WO   2022047231 A1   3/2022

OTHER PUBLICATIONS

Nef et al (The Method of Oxidation and the Oxidation Products of L-Arabinose and of L-Xylose in Alkaline Solutions With Air and With Cupric Hydroxide, pp. 1638-1652, Published Jun. 1917) (Year: 1917).*
Mirescu et al. (A New Environmental friendly method for the preparation of sugar acids via catalytic oxidation of gold catalysts, Applied Catalysis B: Environmental 70, pp. 644-652, Published Jun. 2006) (Year: 2006).*
PCT; App. No. PCT/US2021/048057; International Search Report and Written Opinion dated Dec. 9, 2021.

* cited by examiner

*Primary Examiner* — Yevgeny Valenrod
*Assistant Examiner* — Blaine G Doletski
(74) *Attorney, Agent, or Firm* — Ryan L. Marshall; Barnes & Thornburg LLP

(57) ABSTRACT

Efficient methods of producing L-threonic acid from L-xylonic acid are disclosed.

11 Claims, No Drawings

METHODS FOR THE PRODUCTION OF L-THREONIC ACID SALTS FROM L-XYLONIC ACID

This application is a National Stage application of International Application No. PCT/US2021/048057 filed Aug. 27, 2021, which claims the benefit of U.S. Provisional Application No. 62/706,632, filed Aug. 28, 2020.

TECHNICAL FIELD

The present disclosure relates to a process of producing high purity L-threonic acid salts from L-xylonic acid, comprising providing L-xylonic acid, decarboxylating L-xylonic acid to produce L-threose, and oxidizing the L-threose to produce L-threonic acid salts. The present disclosure also relates to the recycle of unreacted materials within the process.

BACKGROUND

L-Threonic acid is a valuable commercial sugar acid, salts of which are employed in pharmaceutical and supplement preparations. Magnesium and calcium L-threonates in particular have been an important product in the supplement industry. Salts of L-threonic acid are traditionally produced from ascorbic acid by alkaline degradation or peroxide decarboxylation as in U.S. Pat. Nos. 4,822,816, 4,968,716, and Chinese Patent Nos. 1,267,662A, and 106,083,567A. As these methods use costly reagents, have poor selectivity, and are carried out in dilute solutions, there remains a need to produce high purity L-Threonic acid salts in a selective manner from readily available raw materials.

SUMMARY

A method has now been found for the preparation of L-Threonic Acid Salts, this being the object of the present invention, which is characterized in that it comprises the following stages: L-xylonic acid is provided and decarboxylated to yield L-threose; the L-threose is oxidized to L-threonic acid, preferably using a noble metal catalyst, and more preferably after the removal of unreacted acid. Preferably the method comprises the following recycle steps to minimize waste and reduce operating cost: the separation of unreacted L-xylonic acid from the L-threose, and reuse as a raw material for L-threose production, preferably eluting the reaction products through a separation zone containing cation exchange resin.

DETAILED DESCRIPTION

Definitions

As used herein, the term L-xylonic acid refers to the aldonic acid L-xylonic acid, and salts thereof. A salt of L-xylonic acid is referred to as a L-xylonate. For example the sodium salt of L-xylonic acid is sodium L-xylonate.

As used herein, the term L-threose refers to L-threose. L-threose is a rare sugar and is currently not produced industrially.

As used herein, the term KLG refers to the 2-keto-L-gulonic acid, and salts thereof. A salt of 2-keto-Lgulonic acid is referred to as a 2-keto-L-gulonate. For example the sodium salt of 2-keto-L-gulonic acid is sodium 2-keto-L-gulonate. KLG is an intermediate in ascorbic acid production.

As used herein, the term L-sorbose refers to the ketose L-sorbose. L-sorbose is an intermediate in ascorbic acid production.

As used herein, the term metal hydroxide refers to a hydroxide salt of sodium, potassium, lithium, magnesium, or calcium.

The term "decarboxylation" as used herein refers to the removal of a carboxyl group (—COON) by a chemical reaction or physical process. Typical products of a decarboxylation reaction may include carbon dioxide ($CO2$) or formic acid.

The term "electrochemical" refers to chemical reactions that take place at the interface of an electrical conductor (an electrode) and an ionic conductor (the electrolyte). Electrochemical reactions can create a voltage potential between two conducting materials (or two portions of a single conducting material), or can be caused by application of external voltage. In general, electrochemistry deals with situations where an oxidation and a reduction reaction is separated in space.

The term "electrolytic" as used herein refers to an electrochemical oxidation or reduction reaction that results in the breaking of one or more chemical bonds. Electrolytic reactions as used herein preferably describe reactions occurring as a product of interaction with a cathode or anode.

Providing L-Xylonic Acid

The present method requires providing L-xylonic acid as a raw material for the production of L-threonic acid. L-xylonic acid can be produced through different routes, for instance by oxidation of L-sorbose as in Isbell et al., J. Res. Nat. Bur. Stand. 29 (1942) 227-232 and U.S. Pat. No. 6,894,199 B2. KLG can be decarboxylated to yield xylonic acid in good yields using alkaline hydrogen peroxide as in Isbell et al. Carbohydr. Res. 36 (1974) 283-291, and U.S. Pat. No. 6,894,199 B2. L-xylose, like all aldoses, can be oxidized to its corresponding aldonic acid, L-xylonic acid, via noble metal catalysis. KLG can also be decarboxylated electrochemically to produce L-xylonic acid.

Xylonic Acid Decarboxylation

Aldonic acids can be decarboxylated using various chemical systems including hypochlorous acid, and hydrogen peroxide systems, as in U.S. Pat. No. 5,714,602. Aldonic acids can be selectively decarboxylated to yield sugars having one less carbon, using electrochemical cells as in U.S. Pat. Nos. 7,598,374, 7,955,489, and 9,702,047. For example, U.S. Pat. No. 7,955,489, describes the electrolytic decarboxylation of aqueous D- or L-arabinonic to yield erythrose. The electrochemical decarboxylation of sugar acids is a two-electron oxidation.

In one embodiment of the current disclosure, the step of xylonic acid decarboxylation is performed using an electrochemical cell. Preferably the electrochemical cell comprises and anode, cathode, and cation exchange membrane which separates the anode chamber and the cathode chamber. In one embodiment the L-xylonic acid is provided in the cell by the concurrent electrochemical decarboxylation of KLG.

L-Threose Oxidation

Aldoses can be selectively oxidized to aldonate salts by chemical oxidation. Nobel metal catalysts have been widely described in the literature, and gold catalysts in particular have shown to be very effective for this oxidation as described by Theilecke, et al, Catalysis Today, 115-120 (2007). L-Threose has been oxidized to the magnesium L-threonate as described in PCT Application No. PCT/US2020/070085.

In one embodiment of the current disclosure, the step of L-threose oxidation is performed using pressurized oxygen or air in the presence of a metal hydroxide. Preferably the oxidation is performed using a gold-based catalyst. More preferably more than 95% of the L-threose is converted to L-threonic acid.

Threose Purification

Mixtures of sugars, sugar acids and polyols are often separated chromatographically, and industrially using simulated moving bed chromatography. A separation zone containing cation exchange resin can be used as the chromatographic medium, with various cation species result in different sugar elution rates. Calcium has widely been used to separate glucose and fructose, and galactose and tagatose, as in U.S. Pat. Nos. 3,416,961, 4,472,203, 8,802,843. Sodium has been used to separate glycerol and erythritol, as in U.S. Pat. No. 6,030,820.

In one embodiment of the current disclosure, a solution of L-threose and L-xylonic acid produced from the electrochemical decarboxylation of L-xylonic acid is eluted through a separation zone containing cation exchange resin. Water is the eluent and two product solutions are collected, one consisting primarily of L-threose and the other consisting primarily of acids. Preferably the cation exchange resin is in the same cationic form as the acids.

EXAMPLES

Example 1

A 2 Molar solution of xylonic acid was provided. This solution was used as the anolyte of a flow through electrochemical cell comprising a graphite foil anode, cation exchange membrane, and stainless steel cathode. The catholyte was a 3.5 molar solution of potassium hydroxide. The temperature of the anolyte was maintained at 31° C. A current of 90 mA/cm2 of geometric electrode surface was applied to the cell. Neutralization of the anolyte was maintained by addition of potassium hydroxide to the anolyte. The cell was run for 6.8 hrs. At the end of the reaction, there was 932 mmoles of L-xylonic acid, and 694 mmoles of L-threose.

Example 2

A 2 Molar solution of potassium 2-keto-L-gulonic was provided with a pH of 6. This solution was used as the anolyte of a flow through electrochemical cell comprising a graphite foil anode, cation exchange membrane, and stainless steel cathode. The catholyte was a 3.5 molar solution of potassium hydroxide. The temperature of the anolyte was maintained at 45° C. A current of 100 mA/cm2 of geometric electrode surface was applied to the cell. Neutralization of the anolyte was maintained by addition of potassium hydroxide to the anolyte. The cell was run for 19.5 hrs. At the end of the reaction, there was 5.4 mmoles of KLG, 254 mmoles of L-xylonic acid, and 577 mmoles of L-threose.

Example 3

350 ml of a 50 gram per liter solution of L-threose was provided from the electrochemical decarboxylation of KLG and added to a 1 L stirred tank pressure vessel. 2.8 g of a 4.5% gold catalyst, and 9.78 g of Magnesium Hydroxide were added to the solution. The vessel was purged once with oxygen and then pressurized to 100 psi with oxygen and stirred. The reaction was stopped after 3 hours. 98.6% of the L-threose was converted to magnesium L-threonate.

Example 3

A 2 liter column was prepared and filled with cation resin Diaion UBK550 in the potassium form and maintained at 70° C. 150 ml of 25% brix solution of L-threose and L-xylonic acid was provided from an electrochemical decarboxylation and eluted with water at 0.54 bed volumes per hour. The % brix of the elution was measured using refractive index. The L-threose and L-xylonic acid were baseline resolved, and the L-threose fraction was collected from which 98% of the acids had been removed.

Statements

1) A method of producing L-threonic acid from L-xylonic acid comprising: providing L-xylonic, decarboxylating L-xylonic acid to L-threose, and oxidizing the L-threose to L-threonic acid.

2) The method of statement 1 wherein the L-xylonic acid is produced from the chemical decarboxylation of L-sorbose, or KLG.

3) The method of statement 1 wherein the L-xylonic acid is produced from the oxidation of L-xylose.

4) The method of statement 1 wherein the L-xylonic acid is decarboxylated to threose using hypochlorous acid or hydrogen peroxide.

5) The method of statement 1 wherein the L-xylonic acid is decarboxylated to threose in an electrochemical cell.

6) The method of statement 5 wherein the L-xylonic acid is provided by the concurrent decarboxylation of KLG.

7) The methods of any one of statements 1-6 wherein the L-threose is oxidized to L-threonic acid using a catalyst in the presence of oxygen and a metal hydroxide.

8) The methods of statement 7 wherein the catalyst is gold-based.

9) The methods of any one of statements 1-8 wherein the threose is purified by eluting the decarboxylation solution through a separation zone containing cation exchange resin.

We claim:

1. A method of producing L-threonic acid from L-xylonic acid comprising: decarboxylatinq 2-keto-L-gulonic acid (KLG) to L-xylonic acid, decarboxylating the L-xylonic acid to L-threose, and oxidizing the L-threose to L-threonic acid,
wherein the decarboxylatinq 2-keto-L-gulonic acid (KLG) to L-xylonic acid and the decarboxylatinq L-xylonic acid to L-threose is performed concurrently in an electrochemical cell.

2. The method of claim 1 wherein the L-threose is oxidized to L-threonic acid using a catalyst in the presence of oxygen and a metal hydroxide.

3. The method of claim 2 wherein the catalyst is gold-based.

4. The method of claim 2 wherein the metal hydroxide is selected from the group consisting of sodium hydroxide, potassium hydroxide, lithium hydroxide, magnesium hydroxide, and calcium hydroxide.

5. The method of claim 3 wherein the metal hydroxide is selected from the group consisting of sodium hydroxide, potassium hydroxide, lithium hydroxide, magnesium hydroxide, and calcium hydroxide.

6. The method of claim 2 wherein the oxygen is pressurized oxygen or air.

7. The method of claim 3 wherein the oxygen is pressurized oxygen or air.

8. The method of claim 1 wherein more than 95% of the L-threose is converted to L-threonic acid.

9. The method of claim 2 wherein more than 95% of the L-threose is converted to L-threonic acid.

10. The method of claim 3 wherein more than 95% of the L-threose is converted to L-threonic acid.

11. The methods of any one of claims 1, 2, 3, and 4-10 wherein the L-threose is purified by eluting the decarboxylation solution through a separation zone containing cation exchange resin.

\* \* \* \* \*

UNITED STATES PATENT AND TRADEMARK OFFICE
CERTIFICATE OF CORRECTION

| | | |
|---|---|---|
| PATENT NO. | : 11,999,687 B2 | Page 1 of 1 |
| APPLICATION NO. | : 18/042950 | |
| DATED | : June 4, 2024 | |
| INVENTOR(S) | : Jonathan Stapley et al. | |

It is certified that error appears in the above-identified patent and that said Letters Patent is hereby corrected as shown below:

In the Claims

Claim 1, Line 39: delete "decarboxylatinq" and insert --decarboxylating--.
Claim 1, Line 43: delete "decarboxylatinq" and insert --decarboxylating--.
Claim 1, Line 44: delete "decarboxylatinq" and insert --decarboxylating--.

Signed and Sealed this
Twenty-third Day of July, 2024

Katherine Kelly Vidal
*Director of the United States Patent and Trademark Office*